(12) United States Patent
Hodel et al.

(10) Patent No.: US 10,383,690 B2
(45) Date of Patent: *Aug. 20, 2019

(54) MEDICAL LASER USER INTERFACE

(71) Applicant: Boston Scientific Scimed, Inc., Maple Grove, MN (US)

(72) Inventors: Michael R. Hodel, Fremont, CA (US); Terry J. Smith, Menlo Park, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/291,624

(22) Filed: Oct. 12, 2016

(65) Prior Publication Data

US 2017/0027644 A1 Feb. 2, 2017

Related U.S. Application Data

(63) Continuation of application No. 12/120,550, filed on May 14, 2008, now Pat. No. 9,486,286.

(Continued)

(51) Int. Cl.
*A61B 18/22* (2006.01)
*A61B 17/00* (2006.01)
(Continued)

(52) U.S. Cl.
CPC .............. *A61B 18/22* (2013.01); *A61B 34/25* (2016.02); *A61B 2017/00115* (2013.01); *A61B 2017/00973* (2013.01); *A61B 2018/00589* (2013.01); *A61B 2018/00625* (2013.01); *A61B 2018/207* (2013.01); *A61B 2018/225* (2013.01)

(58) Field of Classification Search
None
See application file for complete search history.

(56) References Cited

U.S. PATENT DOCUMENTS 3,769,963 A 11/1973 Goldman
4,388,924 A 6/1983 Weissman et al.
(Continued)

OTHER PUBLICATIONS

Ravina et al., "Arterial Embolization to Treat Uterine Myomata", *Lancet*, 1995; vol. 344: pp. 671-692.
(Continued)

*Primary Examiner* — Lakshmi S Channavajjala
(74) *Attorney, Agent, or Firm* — Bookoff McAndrews, PLLC

(57) ABSTRACT

The medical laser user interface of the present invention generally comprises a medical laser unit and a control system. The medical laser unit includes an optical probe for delivering laser light to a patient's tissue. The control system controls operation of the medical laser unit. Specifically, the control system provides a foot pedal system that enables the user to switch between the delivery of a first wavelength of laser light and a second wavelength of laser light through depression of a foot pedal. In a first embodiment, a single foot pedal can be used to toggle the wavelengths, where as in a second embodiment two foot pedals can be use, one for the first wavelength and one for the second wavelength. The two wavelengths provided include a wavelength for vaporization of tissue and a wavelength for coagulation.

8 Claims, 3 Drawing Sheets

Related U.S. Application Data

(60) Provisional application No. 60/917,751, filed on May 14, 2007.

(51) Int. Cl.
  *A61B 18/20* (2006.01)
  *A61B 34/00* (2016.01)
  *A61B 18/00* (2006.01)

(56) References Cited

U.S. PATENT DOCUMENTS

| | | | |
|---|---|---|---|
| 5,139,494 A | 8/1992 | Freiberg | |
| 5,151,909 A * | 9/1992 | Davenport | B23K 26/06 |
| | | | 359/326 |
| 6,254,601 B1 | 7/2001 | Burbank et al. | |
| 6,267,779 B1 | 7/2001 | Gerdes | |
| 6,506,156 B1 | 1/2003 | Jones et al. | |
| 6,546,933 B1 | 4/2003 | Yoon | |
| 6,550,482 B1 | 4/2003 | Burbank et al. | |
| 6,602,251 B2 | 8/2003 | Burbank et al. | |
| 6,635,065 B2 | 10/2003 | Burbank et al. | |
| 6,638,286 B1 | 10/2003 | Burbank et al. | |
| 7,172,603 B2 | 2/2007 | Burbank et al. | |
| 7,180,922 B2 | 2/2007 | de la Cal | |
| 7,207,996 B2 | 4/2007 | Burbank et al. | |
| 7,223,279 B2 | 5/2007 | Burbank et al. | |
| 7,229,465 B2 | 6/2007 | Burbank et al. | |
| 7,325,546 B2 | 2/2008 | Burbank et al. | |
| 7,329,265 B2 | 2/2008 | Burbank et al. | |
| 8,465,473 B2 | 6/2013 | Horvath | |
| 9,486,286 B2 * | 11/2016 | Hodel | A61B 18/22 |
| 2002/0026225 A1 | 2/2002 | Segal | |
| 2002/0165579 A1 | 11/2002 | Burbank et al. | |
| 2003/0120286 A1 | 6/2003 | Burbank et al. | |
| 2003/0120306 A1 | 6/2003 | Burbank et al. | |
| 2004/0049180 A1 | 3/2004 | Sharps et al. | |
| 2004/0092979 A1 | 5/2004 | Burbank et al. | |
| 2004/0097961 A1 | 5/2004 | Burbank et al. | |
| 2004/0158262 A1 | 8/2004 | Burbank et al. | |
| 2004/0202694 A1 | 10/2004 | Burbank et al. | |
| 2005/0043828 A1 | 2/2005 | Tanaka | |
| 2008/0086117 A1 | 4/2008 | Cao | |

OTHER PUBLICATIONS

Harmanli, MD et al, "Trans-vaginal Uterine Artery Ligation in a Woman with Uterine Leiomyomas", *Journal of Reproductive Medicine*, May 2003, vol. 48; pp. 384-386.

Burbank, et al., "Uterine Artery Occlusion by Embolization or Surgery for the Treatment of Fibroids: A Unifying Hypothesis—Transient Uterine Ischemia," *The Journal of the American Association of Gynecologic Laparoscopists*, Nov. 2000, vol. 7, No. 4 Supplement, pp. S3-S49.

* cited by examiner

MEDICAL LASER USER INTERFACE

PRIORITY CLAIM

The present application is a Continuation of U.S. application Ser. No. 12/120,550, filed May 14, 2008, which claims the benefit of priority of U.S. Provisional Application No. 60/917,751, filed on May 14, 2007, both of which are incorporated by reference herein in their entireties.

FIELD OF THE DISCLOSURE

This invention relates to the field of medical lasers utilizing optical fibers. More specifically, the present invention relates to the function of the control system as well as the use of visual and audible cues to select and confirm selection of a laser power mode.

BACKGROUND OF THE INVENTION

Medical lasers have been utilized in a variety of treatment procedures including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of energy in order to successfully accomplish the desired procedure.

Generally, a surgical probe is utilized to deliver laser energy to the body. The surgical probe generally comprises an optical fiber coupled to a laser source wherein the probe can be positioned such that the tip of the probe is positioned adjacent the targeted tissue. Laser energy is directed out of the tip of the optical fiber onto desired portions of the targeted tissue. The laser optical fiber coupled to the laser source is required to be somewhat flexible such that the optical fiber can be manipulated.

The medical professional performing the particular procedure manipulates the optical fiber into position near the targeted tissue and sets the laser power and mode for vaporization of the targeted tissue. However, there are times when the power and mode settings must be changed from vaporization mode to coagulation mode if there is Needing present and the laser is to be used to stop the bleeding. Lower power settings are also required when treating certain tissue, for example, urethral strictures or bladder tumors. Manually changing between power levels and modes can be time-consuming, especially in the midst of performing treatment. Further, the medical professional performing the medical procedure has to inform the laser operator of the desired power level and mode setting, perhaps alternating a number of times during a single procedure.

Hence, there remains a need for a laser unit providing for smoother, uninterrupted operation during a medical procedure. Further, there remains a need for clarity between the medical professional performing the medical procedure and the laser operator with respect to which power level and mode setting should be operative at any given time.

SUMMARY OF THE INVENTION

The medical laser user interface of the present invention generally comprises a medical laser unit and a control system. The medical laser unit includes an optical probe for delivering laser light to a patient's tissue. The control system controls operation of the medical laser unit. Specifically, the control system provides a foot pedal system that enables the user to switch between the delivery of a first wavelength of laser light and a second wavelength of laser light through depression of a foot pedal. In a first embodiment, a single foot pedal can be used to toggle the wavelengths, where as in a second embodiment two foot pedals can be use, i.e., one for the first wavelength and one for the second wavelength. The two wavelengths provided include a wavelength for vaporization of tissue and a wavelength for coagulation.

The control system also preferably includes another foot-operated control that allows the user to switch between a laser ready mode and a laser standby mode, once again a single pedal or two foot-operated pedals can be used. The control system further preferably includes a touch screen interface that duplicates the operation of the foot pedal controls enabling the user to use one or the other as desired. An audible indication system is also preferably incorporated into the control system whereby the audible indication system notifies the user through audible voice indicators that the medical laser unit is operating in ready mode or standby mode and is delivering the vaporization wavelength or the coagulation wavelength.

A method of the present invention includes the method of operating a medical laser system. As described above, the medical laser system includes a medical laser unit having an optical probe for delivering laser light to a patient's tissue and further includes a foot-operable control system. The method generally includes the steps of depressing a foot pedal to deliver a first wavelength of light from the medical laser unit and depressing the same or a second foot pedal to deliver a second wavelength of light from the medical laser unit. As before, the first wavelength of light is a vaporization wavelength and the second wavelength of light is a coagulation wavelength. The method may additionally include the step of depressing a foot pedal to switch the medical laser unit between a laser ready mode and a laser standby mode.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention, will be more completely understood and appreciated by referring to the following more detailed description of the presently preferred exemplary embodiments of the invention in conjunction with the accompanying drawings of which.

Figure 1:
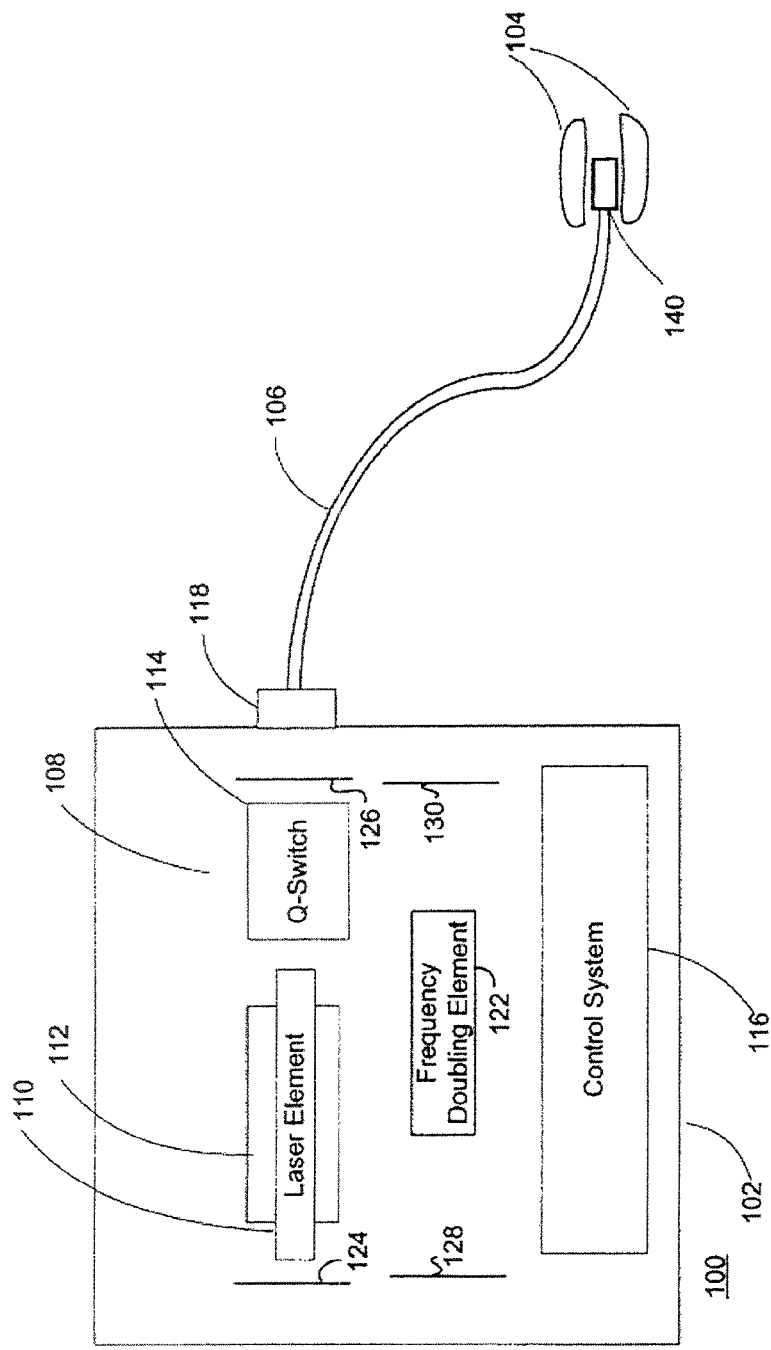
FIG. 1 is a schematic illustration of an embodiment of a laser system with a fiber optic attached to the laser unit.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF EMBODIMENTS OF THE INVENTION

The medical laser system user interface of the present invention is intended to be used with the Greenlight PVP or HPS, a laser system for the treatment of soft tissues, particularly, a laser system for the photoselective vaporization of prostate tissue in the treatment of BPH (benign prostatic hyperplasia). The Greenlight PVP and RFS systems are manufactured by American Medical Systems, Inc. and are generally described in U.S. Pat. Nos. 6,554,824 and 6,986,764, which are hereby incorporated by reference in their entirety. The medical laser user interface system of the present invention is designed to control a high power medical surgical laser providing simple and intuitive controls and indicators. The interface is well suited for surgical procedures where a laser is used to vaporize and coagulate tissue at different laser power levels.

FIG. 1 is a block diagram depicting an exemplary laser system 100 which may be employed for implementing the present invention. Laser system 100 includes a solid-state laser 102, which is used to generate laser light for delivery through optical fiber 106 to target tissue 104. Laser 102 is capable of being operated in a continuous wave or pulsed-mode, wherein the laser light is emitted as macro-pulses having relatively long pulse durations.

Laser 102 more specifically comprises a laser element assembly 110, pump source 112, and frequency doubling crystal 122. In the preferred embodiment, laser element 110 outputs 1064 nm light which is focused into frequency doubling crystal 122 to create 532 nm light. According to one implementation, laser element assembly 110 may be neodymium doped YAG (Nd:YAG) crystal, which emits light having a wavelength of 1064 nm (infrared light) when excited by pump source 112. Laser element 110 may alternatively be fabricated from any suitable material wherein transition and lanthinide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthanum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc laws, flashlamps, and laser diodes.

A Q-switch 114 disposed within laser 102 may be operated in a repetitive mode to cause a train of micro-pulses to be generated by laser 102. Typically the micro-pulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser 102 is provided with a control system 116 for controlling and operating laser 102. Control system 116 will typically include a control processor which receives input from user controls (including but not limited to a beam on/off control, a beam power control, and a pulse duration control, and described in further detail below) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce second harmonic 532 nm green light, and higher harmonics. The frequency doubled, 532 nm wavelength and the shorter wavelength higher harmonic beams are better absorbed by the tissue, and promote more efficient tissue ablation.

In one preferred embodiment the resonant cavity control system is that described in U.S. Pat. No, 5,151,909, which is incorporated by reference as if fully set forth herein.

Laser 102 further includes an output port couplable to optical fiber 106. Output port 118 directs the light generated by laser 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window. Higher harmonic outputs may also be generated from the 1064 nm line, or other line amplified in the laser, including third and fourth harmonics, for shorter wavelengths. Other laser systems may be used, including but not limited to Sapphire lasers, diode lasers, and dye lasers, which are adapted to provide the output power and wavelengths described herein, including wavelengths in the ranges from 200 nm to 1000 nm and from 1100 nm to 1800 nm, for example.

While a bare fiber may be utilized for certain procedures, optical fiber 106 preferably terminates in a tip 140 having optical elements for shaping and/or orienting the beam emitted by optical fiber 106 so as to optimize the tissue ablation process. In the instance of treating BPH, the tip is preferably a side-firing tip.

Figure 2:
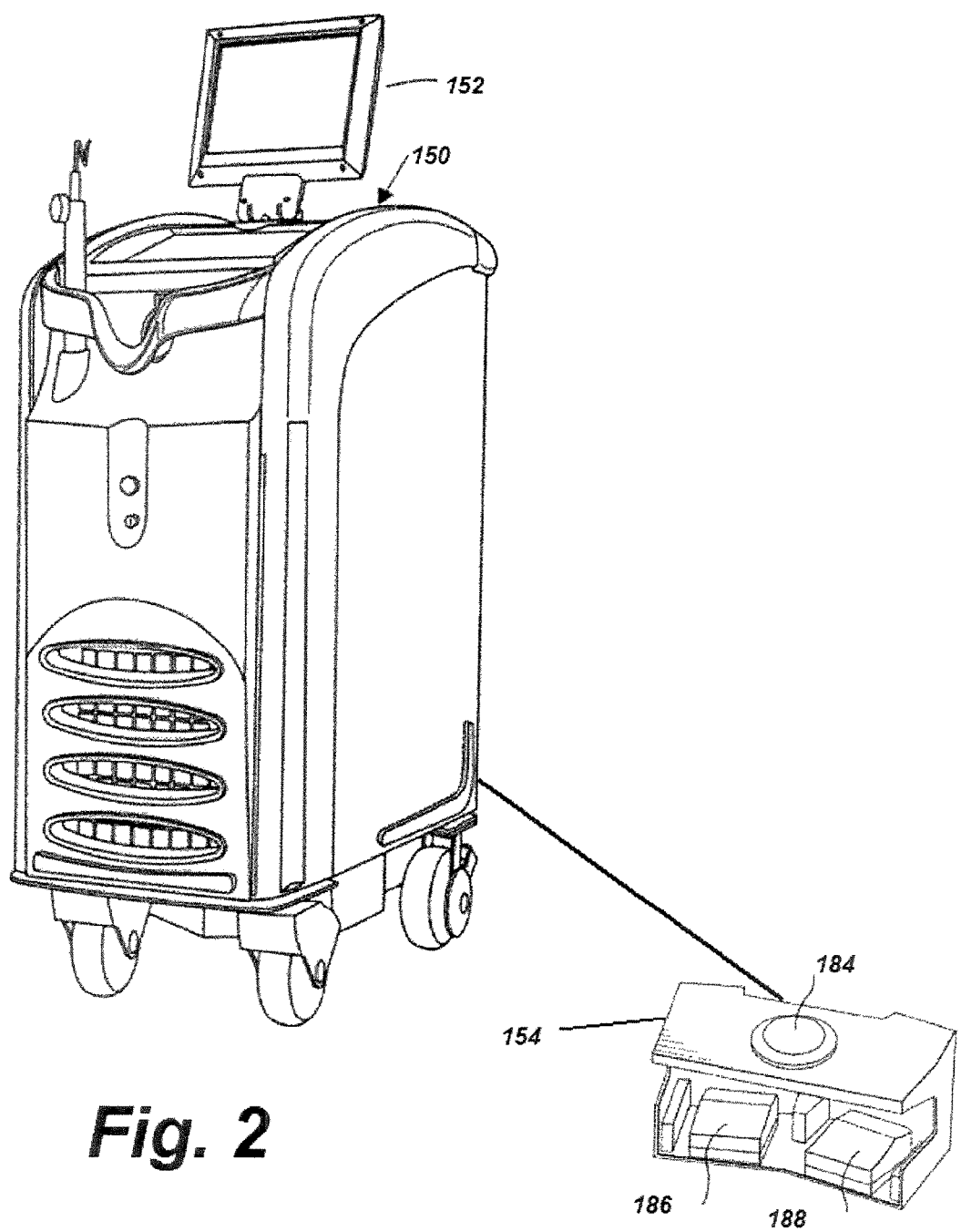
FIG. 2 is a perspective front view of a medical laser user interface system according to an embodiment of the present invention.

Referring to FIG. 2, the laser system 100 is preferably incorporated into a user console 150 and provides the user with a touch screen interface 152 as well as a foot control system 154.

Figure 3:
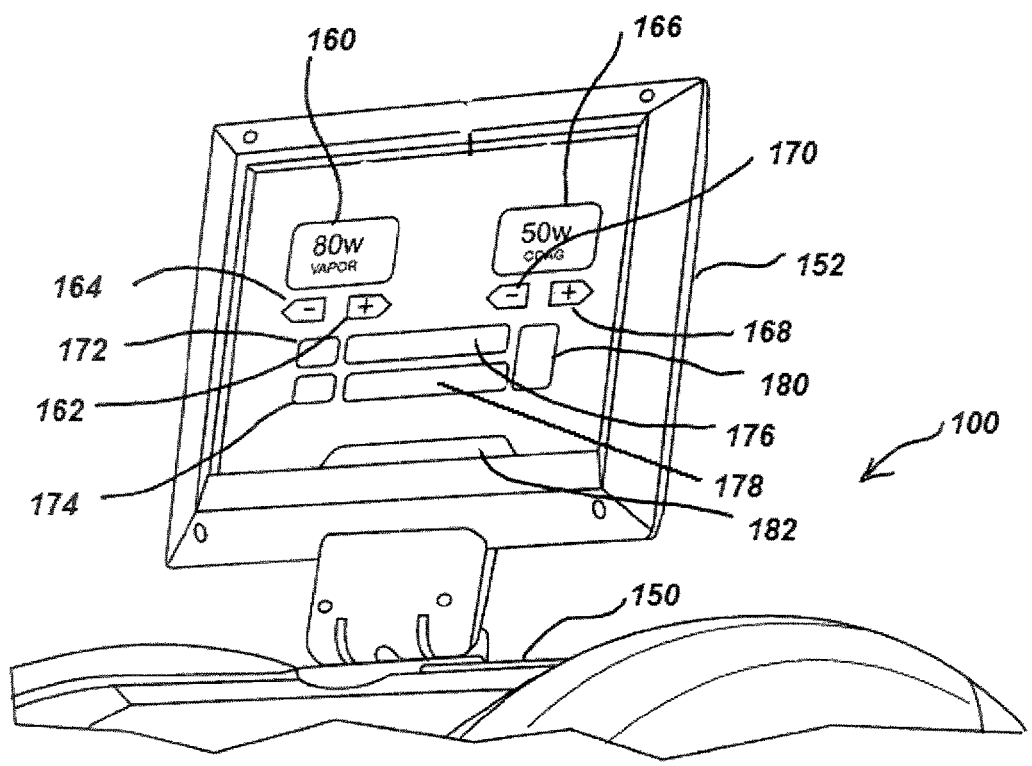
FIG. 3 is a plan view of an embodiment of a control panel display for use with the laser unit of FIG. 2.

The touch screen interface 152 is depicted in detail in FIG. 3. As shown, the touch screen interface 152 preferably includes a vaporization power indicator 160 with corresponding power adjust buttons, (+) 162 and (−) 164 as well as a coagulation power indicator 166 with corresponding power adjust buttons, (+) 168 and (−) 170. The touch screen interface 152 additionally, preferably, includes button controls for READY 172 and STANDBY 174 that also advises the user of which mode is being used by lighting the button controls with indicator lights. Another feature of the touch screen user interface is the ability to provide the user with the lasing time, indicated in box 176, and with an energy indicator, indicated in box 178. A reset button 180, enables the user to reset the energy and lasing time indicators. A set-up button 182 enables the user to adjust set-up parameters.

Referring back to FIG. 2, the foot control system 154 preferably includes a READY/STANDBY button 184 that allows the user to toggle between modes with their foot rather than through use of the READY 172 and STANDBY 174 buttons of the touch screen interface. The foot control system 154 also preferably includes vaporization (VAPOR) pedal 186 and a coagulation (COAG) pedal 188 that enables the user to activate either vaporization or coagulation mode with the touch of their foot rather than through the touch screen 152. In a preferred embodiment, the VAPOR pedal 186 and the COAG pedal 188 are color-coded to the vaporization and coagulation power indicators 160, 166 on the touch screen 152.

In use, the laser system 100, i.e., the GreenLight UPS system, is controlled by the touch screen 152 and the foot pedal system 154. Laser system parameters are selected and the system status is changed by using the touch screen 152. The ready/standby button 184 on top of the foot pedal system 154 may be used to go from READY to STANDBY laser status. An aiming beam from the laser system 100 that accompanies emission from the optical fiber 106 is activated when the laser system 100 is changed from STANDBY to READY and the surgical beam from the optical fiber 106 is activated by pressing the foot pedal, pedal 186 for VAPOR and pedal 188 for COAG.

Power is set by touching the power adjust buttons (162, 164, 168, 170) on the touch screen 152. An audible tone is preferably heard when the maximum or minimum levels are reached. If at any time the laser is unable to deliver the requested power, an alert tone is preferably sounded and the actual power being delivered is displayed in by the vaporization power indicator 160 or the coagulation power indicator 166, as appropriate to the operational mode.

Once the laser system 100 has been started and the set-up parameters have been set (e.g., adjustments to the brightness of the aiming beam, the brightness of the display, the loudness of the volume, etc.), the touch screen 152 preferably prompts the user to attach the optical fiber 106. The user may then select the treatment parameters for vaporization and coagulation by touching the power adjust buttons (162, 164, 168, 170) under the vaporization indicator 160 and the coagulation indicator 166. However, it should be noted that treatment power may be changed at any time by touching the power adjust buttons (162, 164, 168, 170). The laser system 100 has both an automatic joule counter (energy indicator 178) and lasing time indicator 176, which display the accumulated Joules and the lasing time. To reset both counters, the reset button 180 is preferably pressed. The laser system 100 is now configured for operation in a treatment procedure, e.g., vaporization of prostate tissue as treatment for BPH.

To begin the treatment procedure, the READY button 172 is pressed to activate the aiming beam and set up the laser for emission. The READY button 172 preferably changes color, i.e., to orange, to indicate system readiness. Laser energy will now be emitted when one or the other of the footswitches is depressed, pedal 186 for Vaporization and pedal 188 for Coagulation. The aiming beam is preferably provided in a blinking mode during coagulation and in a steady mode during vaporization to provide the physician with yet another indicator as to which mode the laser system 100 is operating in. An audio tone is preferably heard during emission so that the physician is aware that the laser is emitting, different tones for vaporization and coagulation are preferably used to provide the physician with still another indicator of which mode the laser system 100 is operating in. Additionally, an audio indicator is preferably provided announcing the words corresponding to transitions of the laser system from STANDBY, READY, VAPORIZATION and COAGULATION.

Upon ending a procedure, the laser system 100 will preferably return to a STANDBY mode after a number of minutes, e.g., two minutes, without any laser emissions. To go back to STANDBY manually, the STANDBY button. 174 on the touch screen 152 can be depressed or the READY/STANDBY footswitch 184 can be pressed. This will disable laser emission and will turn off the aiming beam.

In view of the above, the laser system 100 provides uncomplicated and intuitive controls/indicators in the form of both visual and audible cues, to simplify use of the laser system 100 by the medical professional. These visual and audible cues ensure that the physician has positive indicator for the selected mode even when the laser console is not directly in the visual field of the surgeon.

The medical laser user interface of the present invention provides the user with the ability to rapidly switch between vaporization and coagulation by simply pressing the corresponding foot pedal; a significant improvement over previous laser system that required a single power control to be adjusted when switching between these modes. In previous systems, a dedicated laser operator would be required to make these adjustments at the laser console incurring the additional expense of the dedicated operator and increasing the opportunity for miscommunication between physician and operator. These drawbacks of previous systems have now been substantially eliminated.

Further, footswitch control of vaporization, coagulation, and ready/standby modes provides complete control of these functions without the need to access corresponding controls on the laser console itself, which is typically located outside the sterile field.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

The invention claimed is:

1. A laser system comprising:
    a single laser switchable between:
        a ready mode for discharge of an aiming laser light,
        a vaporization mode for discharge of a vaporization laser light,
        a coagulation mode for discharge of a coagulation laser light, and
        a standby mode; and
    a foot-operated input device including:
        a first pedal operable to switch the single laser into the vaporization mode,
        a second pedal operable to switch the single laser into the coagulation mode, and
        a button operable to switch the single laser between the ready and standby modes.

2. The system of claim 1, wherein the aiming laser light is in a first state when the single laser is switched into the coagulation mode, and a second state when the single laser is switched into the vaporization mode.

3. The system of claim 2, wherein the aiming laser light is discharged periodically in the first or second state.

4. The system of claim 2, wherein the laser system outputs a first audio signal responsive to actuating the first pedal and a second audio signal responsive to actuating the second pedal, and the second audio signal is different from the first audio signal.

5. The system of claim 2, wherein the button changes color when switched into the ready mode.

6. The system of claim 2, wherein the first and second pedals are configured to permit rapid switching between the vaporization and coagulation modes.

7. The system of claim 2, further comprising a hand-operated input device operable to adjust a power level of the vaporization laser light and a power level of the coagulation laser light.

8. The system of claim 2, wherein the single laser automatically switches into the standby mode after a period of time without discharge of the vaporization laser light or the coagulation laser light.

* * * * *